United States Patent [19]
Popoff et al.

[11] 3,976,648

[45] Aug. 24, 1976

[54] PYRIDINE ADDUCTS OF OXAZOLIDINE AND THIAZOLIDINE-DERIVED CARBODITHIOATES

[75] Inventors: Ivan Christoff Popoff, Ambler; Paul Gordon Haines, Lafayette Hill, both of Pa.

[73] Assignee: Pennwalt Corporation, Philadelphia, Pa.

[22] Filed: Jan. 24, 1975

[21] Appl. No.: 543,746

Related U.S. Application Data

[60] Division of Ser. No. 438,819, Feb. 1, 1974, Pat. No. 3,943,143, which is a continuation-in-part of Ser. No. 356,034, April 30, 1973, abandoned, which is a continuation-in-part of Ser. No. 259,900, June 5, 1972, abandoned, which is a continuation-in-part of Ser. No. 116,250, Feb. 17, 1971, Pat. No. 3,674,701.

[52] U.S. Cl. .......................................... 260/270 PY
[51] Int. Cl.² .............. C07D 417/02; C07D 413/02
[58] Field of Search ............. 260/299,270 PY, 260/787

[56] References Cited
UNITED STATES PATENTS 3,943,143    3/1976    Popoff ............................... 260/270

*Primary Examiner*—Alton D. Rollins
*Assistant Examiner*—Mark L. Berch

[57] ABSTRACT

Oxazolidine and thiazolidinecarbodithioates, and pyridine adducts thereof, are accelerators for the vulcanization of EPDM elastomers, wherein they exhibit non-blooming characteristics.

15 Claims, No Drawings

PYRIDINE ADDUCTS OF OXAZOLIDINE AND THIAZOLIDINE-DERIVED CARBODITHIOATES

This application is a division of copending application Ser. No. 438,819, filed Feb. 1, 1974, now U.S. Pat. No. 3,943,143, which is a continuation-in-part of application Ser. No. 356,034, filed Apr. 30, 1973, now abandoned, which is a continuation-in-part of application Ser. No. 259,900, filed June 5, 1972, now abandoned, which in turn is a continuation-in-part of application Ser. No. 116,250, filed Feb. 17, 1971, now U.S. Pat. No. 3,674,701.

This invention relates to compounds which are active accelerators for the vulcanization of elastomers, and more particularly to zinc oxazolidinecarbodithioates and zinc thiazolidinecarbodithioates and their pyridine adducts which are especially useful in retarding surface bloom in vulcanized elastomers, especially in elastomeric terpolymers of ethylene, propylene and a dienemonomer (EPDM elastomer).

In the process of vulcanization of elastomers using an accelerator in conjunction with sulfur or other vulcanization agent, there has been a need for a non-blooming type of accelerator that has adequate accelerator activity. Zinc dithiocarbamates, such as zinc dimethyl-and diethyldithiocarbamate, have high activity as accelerators but they give an undesirable surface bloom on elastomer vulcanizates. Surface bloom is a disadvantageous phenomenon characterized by the appearance of a coating of solids or oil upon the surface of a vulcanizate as a result of the migration to the surface of one or more of the components of the vulcanized elastomer. This may occur quickly, as for example, in a few days or a week. Blooming is also particularly a problem in the case of EPDM elastomers, which are terpolymers of ethylene, propylene and diene-monomer, for example, 11-ethyl-1, 11-tridecadiene, 1,5-cyclooctadiene, 1,5-hexadiene, 5-ethylidene-2-norbornene, 5-methylene-2-norbornene, dicyclopentadiene, 2,5-norbornadiene and the like. Moreover, the curing of the EPDM elastomer requires a high activity accelerator because of the low level of unsaturation in the polymer.

U.S. Pat. No. 3,674,701 discloses a non-blooming accelerator composition comprised of a mixture of a certain thiourea compound with the zinc salt of the reaction product of essentially equimolar amounts of ethanolamine, formaldehyde and carbon disulfide. We have now managed to isolate, through solvent extractions and crystallizations, a particular novel compound from said complex reaction product mixture, which, by itself, is a non-blooming accelerator, that is, a thiourea or other adjunct is not required to be mixed therewith for good results in EPDM elastomer vulcanization. This invention embodies this novel compound and the class of related oxazolidinecarbodithioates and thiazolidinecarbodithioates which have surprising non-blooming accelerator activity.

The compound of this invention is represented by the structure

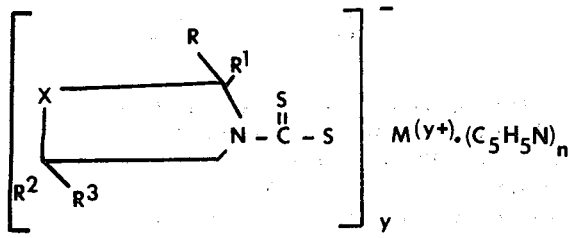

where X is sulfur or oxygen, R, R¹, R², and R³ are independently selected from the group consisting of hydrogen, lower alkyl (e.g., having from 1 to 8 carbon atoms, and preferably methyl); $CCl_3$, phenyl, and substituted phenyl wherein there are one or more substituents selected from the group consisting of $NR^4R^5$, OH, $OR^4$ and Cl where $R^4$ and $R^5$ are independently selected from the group consisting of hydrogen and lower alkyl ($C_1$–$C_8$); $C_5H_5N$ represents a pyridine molecule and $n$ is an integer of zero to 5, preferably 0 to 3, the higher values of $n$ resulting from acidic characteristics of the substituents; M is selected from the group consisting of sodium, potassium, zinc, cadmium, copper, iron, tri-(lower) alkyl substituted ammonium, and phenyl-di-(lower) alkyl substituted ammonium; and $y$ is an integer of 1 to 3, depending on the valency of the M (ion). The preferred M ions are zinc and triethyl ammonium.

A convenient method of preparing the compounds of this invention is to first prepare an oxazolidine or thiazolidine (or substituted derivative thereof), represented by the formula

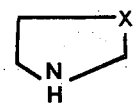

(where X is oxygen or sulfur) involving the reaction of an amino alcohol or an amino mercaptan with an aldehyde or ketone. When formaldehyde is used, the resulting intermediary triazine is pyrolized at about 100° to 200°C., in accordance with the procedure suggested by A. Paquin, Ber. 82, 316 (1949). A typical preparation of the unsubstituted oxazolidine is as follows, employing the reaction scheme as shown:

EXAMPLE 1

Preparation of Oxazolidine from 1,3,5-tris(2-hydroxyethyl)hexahydro-1,3,5-triazine

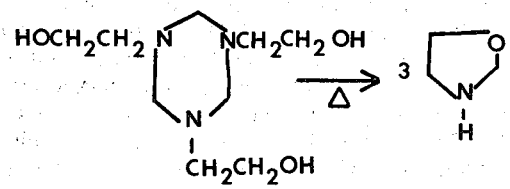

With stirring, 486 g. (6.0 moles) of 37% formaldehyde solution was added dropwise to 366 g. (6.0 moles) of ethanolamine at 40° – 45°C. After an additional hour at 40° – 45°C the water was removed in a rotary vacuum evaporator at 50° – 55°C to leave a residue of 447 g. amber cooled oil as the 1,3,5-tris(2-hydroxyethyl)-hexahydro-1,3,5-triazine containing 18.98% N (calc. 19.17% N).

A 24.1 g. portion of the above triazine was distilled in a Pyrex glass-still having distillate receiver cooled by a Dry Ice-acetone bath (−75°C). Vapor temperature was 52° – 69°C at 1.2 mm. pressure. The still-pot temperature was 118° – 139°C. Temperature of the oil bath surrounding the stillpot was 153° – 172°C. The distillate was 22.2 g. of colorless oxazolidine (very viscous at −75°C).

The oxazolidinecarbodithioates and thiazolidinecarbodithioates of this invention are obtained by reacting an oxazolidine (or thiazolidine) with carbon disulfide and the desired metal salt, or metal oxide, or amine, at about 0° to 100°C. in an appropriate solvent such as pyridine, triethylamine, tributylamine, methanol, isopropanol, ethanol and butanol, desirably containing a minor proportion of a basic amine such as triethylamine, tributylamine, pyridine, dimethylaniline and diethylaniline. The preferred solvent system, however is pyridine, which acts not only as the reaction medium but provides the desired basicity. The products of the reaction will then generally be recovered as a pyridine adduct thereof, containing as many as five molecules of pyridine. The pyridine can usually be removed from the zinc salt by heating the adduct up to about 50° to 150°C under reduced pressure, but this is not necessary since the presence of the pyridine in the salt does not in anyway impede the good performance of the compounds as non-blooming vulcanization accelerators. The following examples illustrate the preparation of representative compounds of this invention.

EXAMPLE 2

Preparation of Zinc Bis(3-oxazolidinecarbodithioate)

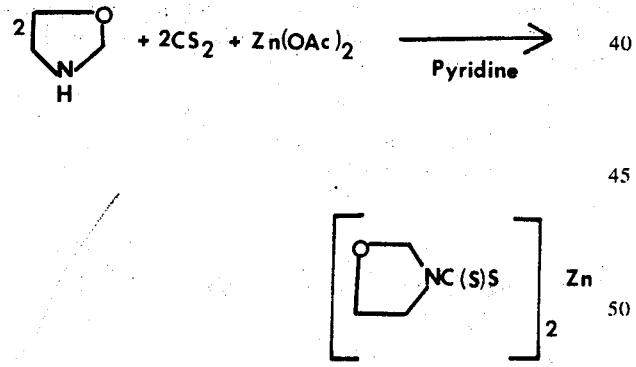

With stirring and cooling to maintain 15° – 25°C. 111.1 g. (1.52 mole) of freshly distilled, cold oxazolidine [prepared from 1,3,5-tris(2-hydroxyethyl)hexahydro-1,3,5-triazine, as described by A. Paquin, Chem. Ber. 82, 316 (1949) was added to a mixture of 600 g. pyridine, 116 g. (1.52 moles) carbon disulfide and 139.5 g. (0.76 mole) anhydrous zinc acetate. After standing overnight at room temperature, the precipitated product was filtered, water-washed and air-dried to give 193.5 g. of a mono pyridine adduct, m.p. 195° – 200°C (decomp.); dilution of the filtrate with water gave an additional 34.4 g. (total conversion 68.3%).

Vacuum-drying of the pyridine adduct at 80° – 85°C removed the pyridine (weight loss indicates a 1:1 mole ratio of pyridine to zinc salt to give the desired zinc bis(3-oxazolidinecarbodithioate), a white, crystalline product melting at 223° – 225°C (decomp.). It had the following analysis:

Found: C, 26.75; H, 3.46; N, 7.63; Zn, 17.9%. Calcd for $C_8H_{12}NO_2S_4Zn$: C, 26.56; H, 3.32; N, 7.75; Zn, 18.10%.

EXAMPLE 3

Preparation of Zinc Bis(2-trichloromethyl-3-oxazolidinecarbodithioate)

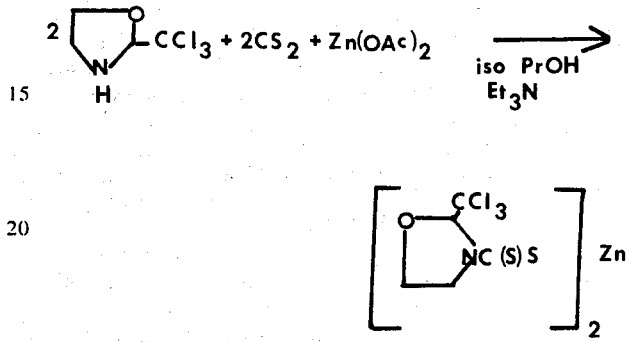

95 2/10 g. of 2-trichloromethyloxazolidine (preparation described by W. Ruske and I. Hartmann, J. Prakt, Chem. 18, 146 (1962)) was dissolved in a mixture of 300 ml isopropanol, and 50.5 g. (0.50 mole) of carbon disulfide was added dropwise followed by 43.9 g. (0.25 mole) of anhydrous zinc acetate. The reaction mixture was heated for 2 hours at 45° – 50°C, cooled to room temperature, and diluted with 1 liter water; the precipitated product was filtered, washed thoroughly with water and dried in vacuo to give 86.3 g. of the crude product, melting at 193° – 195°C (decomp.). Hot benzene extractions of the crude product gave 38 g. of the desired carbodithioate sintering at 208°C, and melting 213° – 216°C (decomp.). It had the following analysis:

Found: C, 20.19; H, 2.08; N, 4.67; S, 20.96%. Calcd for $C_{10}H_{10}Cl_6N_2O_2S_4Zn$: C, 20.12; H, 1.68; N, 4.69; S, 21.46%.

EXAMPLE 4

Preparation of Zinc Bis (2-trichloromethyl-3-oxazolidinecarbodithioate) Pyridine Adduct

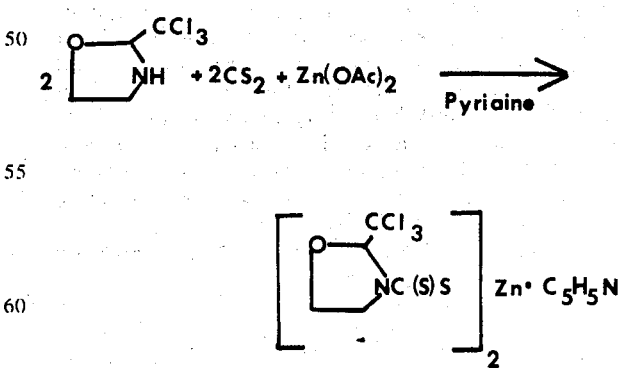

30 4/10 grams (0.160 mole) of 2-trichloromethyloxazolidine (preparation described by W. Ruske and I. Hartmann, J. Prakt, Chem. 18, 146 (1962)) was dissolved in 480 g. of pyridine. With rapid stirring at room temperature, 14.4 g. (0.184 mole) of carbon disulfide was added dropwise followed by 15.2 g. (0.083 mole) of anhydrous zinc acetate. The reaction mixture was heated 3 hours at 45° - 50°C, cooled to room temperature, and then diluted with 1 liter water; the precipitated product was filtered and dried in vacuo at room temperature to obtain 33.4 g. of the desired pyridine adduct melting at 205° - 207°C (decomp.). A small analytical sample, recrystallized in methanol, sintered at 209°C and melted with decomposition at 212°-214°C. It had the following analysis:

Found: C, 26.70; H, 2.74; N, 6.30; S, 19.60; Cl, 31.37; Zn, 9.55%. Calcd for $C_{10}H_{10}Cl_6N_2O_2S_4Zn \cdot C_5H_5N$: C, 26.65; H, 2.22; N, 6.23; S, 18.95; Cl, 31.54; Zn, 9.68%.

EXAMPLE 5

Preparation of Zinc Bis (2,2-dimethyloxazolidine-3-carbodithioate)

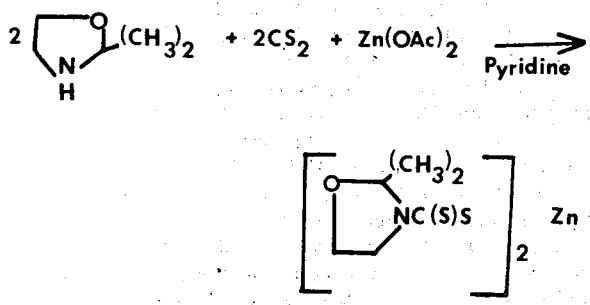

While cooling and stirring, 20 g. (0.20 mole) of 2,2-dimethyloxazolidine (preparation described by E. Bergmann et. al., J. Am. Chem. Soc. 75, 358 (1953)) was added to a solution of 15.2 g. (0.20 mole) carbon disulfide in 150 g. pyridine. To the stirring solution was added 18.3 g. (0.10 mole) of anhydrous zinc acetate at 25° - 30°C. After standing overnight at room temperature, filtration gave 15.2 g. of the crude product; vacuum-concentration of the filtrate and ethanol-dilution of the residue gave an additional 10.4 g. After combining and vacuum-drying of the crude product at 100°C there was obtained 17.8 g. of the desired carbodithioate melting at 188° - 190°C (decomp.). A small sample, dissolved in hot chloroform and precipitated by hexane (m. 192° - 3°C decomp.) had the following analysis:

Found: C, 34.22; H, 4.47; N, 6.84; Zn, 15.20%.

Calcd for $C_{12}H_{20}N_2O_2S_4Zn$: C, 34.50; H, 4.79; N, 6.71; Zn, 15.67%.

EXAMPLE 6

Preparation fo Zinc bis[2-(3-ethoxy-4-hydroxyphenyl)oxazolidine-3-carbodithioate], Tripyridine Adduct

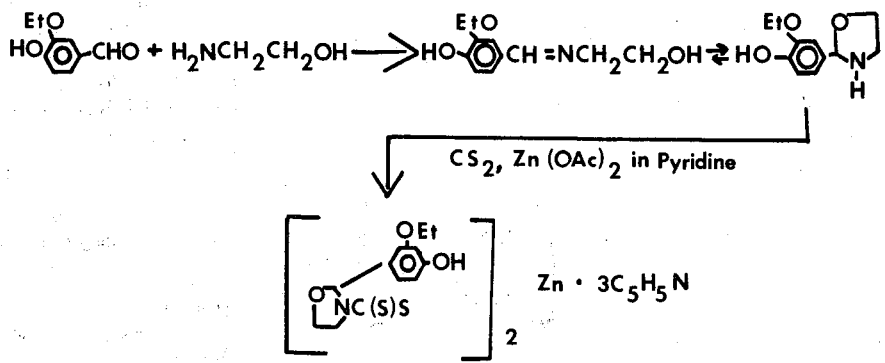

A mixture of 80 ml isopropanol, 15.7 g. (0.094 mole) 3-ethoxy-4-hydroxybenzaldehyde and 6.0 g. (0.098 mole) ethanolamine was heated on the steam bath for 1 hour. Filtration at room temperature gave 19.3 g. of crystals melting at 157° - 160°C. On the basis of its IR spectrum [1650 cm$^{-1}$ for C=N, L. W. Daasch, J. Am. Chem. Soc. 73, 4523, (1951)] the product appeared to be primarily the Schiff Base β-(3-ethoxy-4-hydroxybenzylideneamino)-ethanol which can be in tautomeric equilibrium with the cyclic 2-(3-ethoxy-4-hydroxyphenyl)oxazolidine.

The mixture of the above crystals with 40 g. of pyridine, 7.6 g. (0.10 mole) of carbon disulfide and 9.2 g. (0.050 mole) of anhydrous zinc acetate was heated for 1.5 hours at 50° - 55°C and then left standing overnight at room temperature. Filtration and hexane-washing of the precipitate gave 38.1 g. of the pyridine adduct melting at 106° - 112°C and having the following analysis:

Found: C, 53.25; H, 4.95; N, 7.74; Zn, 7.46%. Calcd for $C_{24}H_{28}N_2O_6S_4Zn \cdot 3C_5H_5N$: C, 53.77; H, 4.94; N, 8.04; Zn, 7.51%.

The IR-spectrum of this product did not show any absorption at 1650 cm$^{-1}$ characteristic of the Schiff Base discussed above. This proved that the Schiff Base tautomerized to the corresponding oxazolidine which in turn reacted with CS$_2$ and Zn(OAc)$_2$.

EXAMPLE 7

Preparation of Zinc Bis[2-(p-dimethylaminophenyl)oxazolidine-3-carbodithioate)], Pyridine Adduct This product was prepared as described in Example 6 using p-dimethylaminobenzaldehyde instead of 3-ethoxy-4-hydroxybenzaldehyde. The evaporation residue was washed with water and the remaining solid was dissolved in dimethylformamide at room temperature. The filtered solution was diluted with water to obtain the product melting at 91° - 93°C (decomp.). Its structure

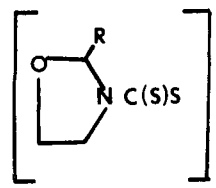 $Zn \cdot C_3H_5N$, where R is 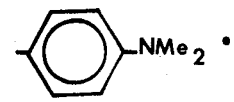

was confirmed by IR spectrum and elemental analysis:
Found: C, 51.72; H, 5.82; Zn, 9.13%. Calcd for C₂₄H₃₀N₄O₂S₄Zn.C₅H₅N: C, 51.30; H, 5.16; Zn, 9.64%.

EXAMPLE 8

Preparation of Zinc Bis(thiazolidine-3-carbodithioate)

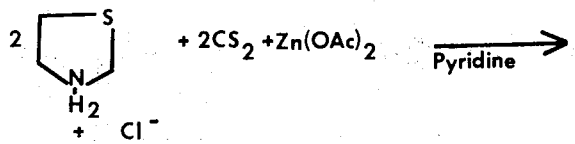

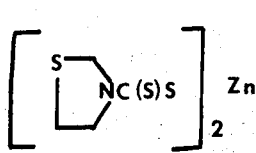

While cooling and stirring 250 g. of pyridine, 175 g. (1.40 moles) of thiazolidine hydrochloride [preparation described by S. Ratner and H. Clarke, J. Am. Chem. Soc. 59, 200 (1937)] was added. After it had dissolved, 106.4 g. (1.40 mole) of carbon disulfide was added dropwise, followed by 128.5 g. (0.70 mole) of anhydrous zinc acetate. The resulting reaction mixture was stirred at 40° – 50°C for 2 hours. The precipitate was filtered at 5° – 10°C. The crude solid was water-washed and finally freed of pyridine by vacuum-drying at 120°C. to give 147.8 g. of the desired product. It gradually decomposed starting at ca. 200°C without a definite final decomposition point. A small sample washed with hot benzene had the following analysis:
Found: C, 24.46; H, 2.95; N, 7.31; Zn, 16.58%. Calcd for C₈H₁₂N₂S₆Zn: C, 24.40; H, 3.05; N, 7.12; Zn, 16.62%.

EXAMPLE 9

Preparation of Zinc Bis[(2-trichloromethyl)thiazolidine-3-carbodithioate]-Dipyridine Adduct

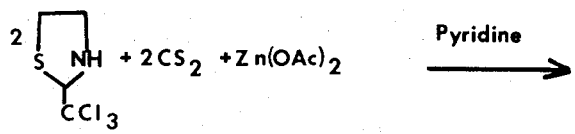

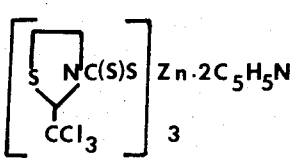

To 158.2 g. (2.0 moles) of pyridine was added 66.0 g. (0.32 mole) of 2-trichloromethylthiazolidine [preparation described by B. Sweetman et al, J. Med. Chem. 12, 888 (1969)] and to the resulting stirred solution at 20°C was added 24.4 g. (0.32 mole) of carbon disulfide over a 10-minute period. The solution was warmed to 25°C, at which temperature 29.4 g. (0.16 mole) of zinc acetate was added portionwise over 0.5-hr. period. The temperature was maintained at 25°C with an ice bath during the addition. The resulting clear amber solution was stirred at ambient temperature for an additional 17 hours. The precipitate, having formed during the additional stirring time, was filtered and washed with 4 × 500 ml of water. After air-drying, 100 g. (79% conversion) of off-white product was obtained. Its melting point was 181° – 3°C with some gas evolution. It had the following analysis:
Found: C, 30.57; H, 3.01; Cl, 27.36; Zn, 8.1%. Calcd for C₁₀H₁₀Cl₆N₂S₆Zn.2C₅H₅N: C, 30.52; H, 2.56; Cl, 27.07; Zn, 8.3%.

EXAMPLE 10

Preparation of Zinc Bis(2,2-dimethylthiazolidine-3-carbodithioate)

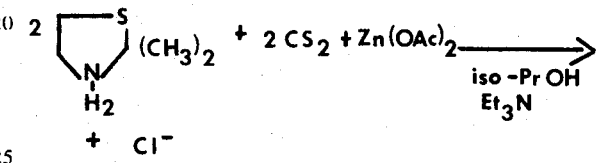

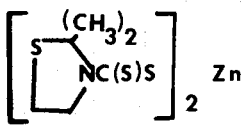

While cooling and stirring at 10°C, 76.8 g. (0.50 mole) 2,2-dimethylthiazolidine hydrochloride [preparation described by B. Sweetman et al, J. Med. Chem. 12, 888 (1969)] was added to a mixture of 30 ml isopropanol and 101 g. (1.00 mole) triethylamine. Likewise, 38.0 g. (0.50 mole) of carbon disulfide was gradually added, followed by 45.8 g. (0.25 mole) of anhydrous zinc acetate. After standing overnight at room temperature, the precipitate was filtered, twice water-washed with 1 liter portions of water and air-dried to give 80.5 g. of the yellow product melting at 148° – 153°C (decomp.) and having the following analysis:
Found: C, 31.51; H, 4.70%. Calcd for C₁₂H₂₀N₂S₆Zn: C, 32.04; H, 4.45%.

EXAMPLE 11

Preparation of Zinc Bis[spiro(cyclohexane-1,2'-oxazolidine)-3-carbodithioate]

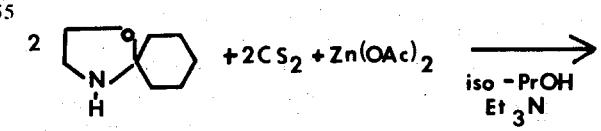

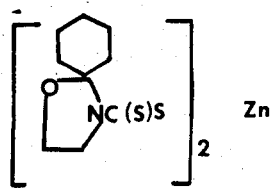

Thirty-eight grams (0.50 mole) of carbon disulfide was added with stirring at 10° – 20°C to a mixture of 500 g. isopropanol and 50.5 g. (0.50 mole) triethylamine. To this solution was added 70.5 g. (0.50 mole) of spiro(cyclohexane-1,2'-oxazolidine) [preparation described by A. Cope and E. Hancock, J. Am. Chem. Soc. 64, 1503 (1942)] followed by 46.0 g. (0.25 mole) of anhydrous zinc acetate. The reaction mixture was stirred 4 hours at room temperature. After overnight standing, the precipitate was filtered to give 97.4 g. of the desired carbodithioate melting at 198° – 200°C (decomp.). A sample, dissolved in hot dimethylsulfoxide and precipitated by addition of methanol, melted at 212° – 213°C and had the following analysis:

Found: C, 42.80; H, 5.41; N, 5.75; Zn, 12.90%. Calcd for $C_{18}H_{28}N_2O_2S_4Zn$: C, 43.43; H, 5.63; N, 5.63; Zn, 13.15%.

An alternate and considerably less preferred method of obtaining the zinc salts embodied in this invention is, as mentioned previously, to isolate the desired compound from the complex reaction product of the aminoalkanol (or aminomercaptan), formaldehyde, carbon disulfide and zinc salt precursor by time-consuming solvent extraction giving generally relatively poor yields. Typical of such a preparation is the following in which the compound of Example 2, zinc bis(3-oxazolidinecarbodithioate), is prepared by the alternate procedure.

EXAMPLE 12

With rapid stirring at 10° – 20°C, 243 g. (3.0 moles) 37% formaldehyde solution was dropwise added to a solution of 183 g. (3.0 moles) ethanolamine in 600 ml of water. The reaction mixture was stirred 1 hour at 50° – 60°C. At 5° – 10°C, 228 g. (3.0 moles) of carbon disulfide was added dropwise. Stirring was continued for two more hours at 40° – 50°C. With rapid stirring at room temperature the reaction mixture was added to a solution of 432 g. (1.5 moles) of zinc sulfate heptahydrate in 900 ml of water. The precipitate was filtered, water washed and air-dried to give 143.3 g. white crystals. (Accelerator No. 15) melting at 162° – 175°C (decomp.), a 26.4% conversion.

The product (7 g) was dissolved in 66 cc hot dimethylformamide, cooled, diluted with 20 cc ethanol and filtered. The solid was treated with 300 cc hot chloroform, filtered hot, cooled, diluted with 300 cc ethanol and filtered to obtain 2.2 g (8.3% yield based on ethanolamine) of zinc bis(3-oxazolidinecarbodithioate) of Example 2, m.p. 221° (decomp.), containing 26.73%C, 3.44%H, 7.96%N. For calcd. values see Example 2.

EXAMPLE 13

Preparation of Zinc Bis(2-methyl-2-phenyloxazolidine-3-carbodithioate) Pyridine Adduct This product was prepared as described for zinc bis[2-(3-ethoxy-4-hydroxyphenyl)oxazolidine-3-carbodithioate]tripyridine adduct (Compound No. 6, Example No. 6) using acetophenone instead of 3-ethoxy-4-hydroxybenzaldehyde. After the reaction was completed, the reaction mixture was evaporated to dryness and the solid residue was thoroughly washed with hot isopropanol. The product, m.p. 169° – 173°C (dec.), was identified by its infrared spectrum. It was contaminated with some zinc acetate.

EXAMPLE 14

Preparation of Zinc Bis(4-morpholinecarbodithioate)

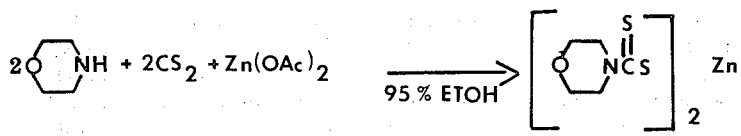

To a stirred mixture of 22.0 g. (0.10 mole) of zinc acetate dihydrate and 15.2 g. (0.20 mole) of carbon disulfide in 400 ml of 95% ethanol was added slowly 17.4 g. (0.20 mole) of morpholine at 20° – 40°C. The reaction mixture was filtered to obtain 34.6 g. of the desired solid product which did not melt at up to 300°C. A portion of it was dissolved in chloroform, reprecipitated with hexane and analyzed.

Found: C, 31.40; H, 4.39; N, 7.30; Zn, 16.00. Calcd for $C_{10}H_{16}N_2O_2S_4Zn$: C, 30.82; H, 4.11; N, 7.19; Zn, 16.80.

The above product is reported to be a rubber accelerator in C. A. 54, 19004 (1960; Russian Patent 127,387 of 3/25/60). No physical properties are given in the abstract, but the above analyses confirmed its composition.

EXAMPLE 15

Zinc Bis(2-phenyloxazolidine-3-carbodithioate), Pyridine Adduct

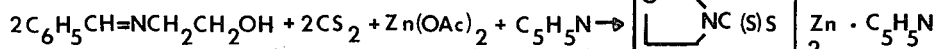

The starting material N-(2-hydroxyethyl)-benzalamine, i.e., the tautomer of 2-phenyloxazolidine was prepared from benzaldehyde and ethanolamine by the method of L. Daasch and H. Hanninen, J. Amer. Chem. Soc. 72, 3673 (1950).

To the stirred solution of 131 g. (0.88 mole) of N-(2-hydroxyethyl) benzalamine, 68.0 g. (0.88 mole) carbon disulfide and 300 ml. pyridine was added 81.0 g. (0.44 mole) of anhydrous zinc acetate. After 5 hours stirring at 25°–45°C. the precipitate was filtered off, washed twice with 700 ml. 95% ethanol, and again filtered to give 217.7 g. of the desired product having a decomposition point of 196°–200°C. The product had the following analysis:

Found: C, 50.75; H, 4.33; N, 7.78; Zn, 11.02. Calc. for $C_{20}H_{20}N_2O_2S_4Zn.C_5H_5N$: C, 50.67; H, 4.22; N, 7.90; Zn, 11.05.

EXAMPLE 16

Zinc Bis(2-phenyloxazolidine-3-carbodithioate)

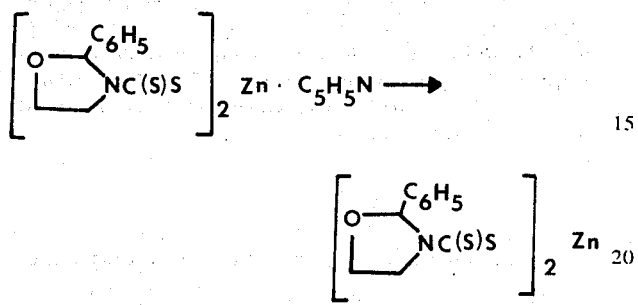

A 50.0 g. sample of the above pyridine adduct of Example No. 15 was heated at 110°–115°C. at 1 mm. Hg pressure for 17 hours to give 44.7 g. of the desired product which melted with decomposition at 133°–186°C. The infrared spectrum and the following analyses showed that the product contained only 5% residual pyridine.

Found: C, 47.84; H, 4.21; Zn, 12.17. Calc. for product containing 5% pyridine: C, 48.29; H, 4.02; Zn, 12.10.

EXAMPLE 17

Zinc Bis[2-(p-chlorophenyl)oxazolidine-3-carbodithioate], Pyridine Adduct

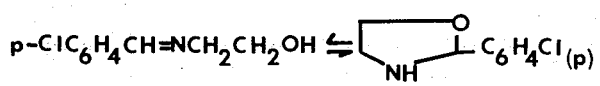

The above tautomeric mixture (m. 70°–73°C.) was prepared from p-chlorobenzaldehyde and ethanolamine in the same manner as that for the ortho-chloro isomer described by L. Daasch and H. Hanninen, J. Amer. Chem. Soc. 72, 3673 (1950).

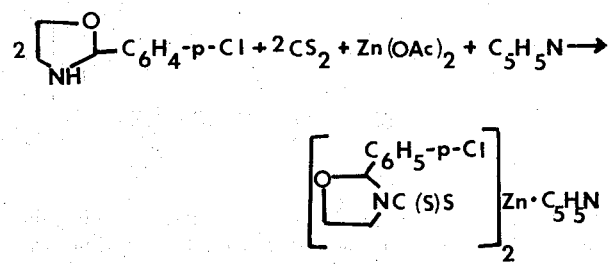

One hundred fourteen grams (0.62 mole) of the above mixture of 2-(p-chlorophenyl)oxazolidine and Schiff Base was added to a solution of 47 g. (0.62 mole) carbon disulfide in 200 ml. pyridine. After standing overnight at room temperature, the pyridine was removed by distillation at 0.5 mm. Hg pressure and pot temperature of 60°C. to leave a residue of 203 g. brown, sticky solid. The crude residue was vigorously washed with water and then with isopropanol to give 132 g. of the desired product, melting at 119°–132°C. with decomposition. It contained 6.00% nitrogen. Theoretical nitrogen content is 6.35%.

EXAMPLE 18

Zinc Bis[2-(1-ethylpentyl)oxazolidine-3-carbodithioate], Pyridine Adduct

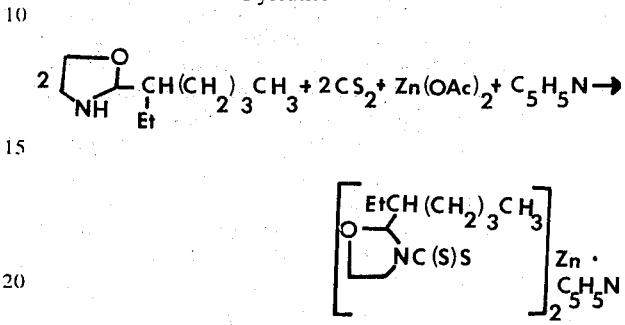

The starting material, i.e., the tautomeric mixture of oxazolidine and Schiff Base, was prepared from 2-ethylhexanal and ethanolamine in benzene by azeotroping the water. The tautomeric mixture was distilled (boiling point 100°–102°C. at 3 mm.) before reacting it with $CS_2$.

To the cooled solution of 127 g. (0.74 mole) of the above 2-(1-ethylpentyl)oxazolidine Schiff Base in 150 ml. pyridine was added 57.0 g. (0.74 mole) carbon disulfide and then 68.0 g. (0.37 mole) anhydrous zinc acetate. After stirring at 45°–50°C. for ½ hour, the reaction mixture was stripped at 60°C. and 1 mm. to leave a residue of 225 g. of semi-solid product having the following analysis:

Found: C, 50.21; H, 7.43; N, 6.79; Zn, 10.53. Calc. for $C_{22}H_{40}N_2O_2S_4Zn.C_5H_5N$: C, 50.91; H, 7.07; N, 6.60; Zn, 10.28.

EXAMPLE 19

Zinc Bis(5-methyl-2-trichloromethyloxazolidine-3-carbodithioate), Pyridine Adduct

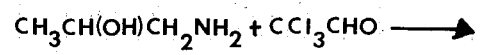

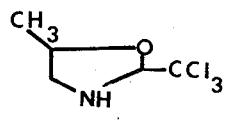

With stirring and cooling, 90.0 g. (1.2 moles) 1-amino-2-propanol was added to 250 ml. glacial acetic acid. After addition of 177.0 g. (1.20 moles) of chloral, the reaction mixture was heated for 1 hour at 45°–50°C. The acetic acid was distilled off at 5 mm. to a pot temperature of 45°C. The oily distillation residue of 236 g. was diluted with 300 cc. of hexane and chilled to 10°C. The precipitate was filtered off to obtain 36 g. of crude 5-methyl-2-trichloromethyloxazolidine, m.p. 46°–54°C. A small sample, twice crystallized from hexane, melted at 59°–62°C. and had the following analysis:

Found: C, 29.77; H, 4.00; N, 7.10. Calc. for $C_5H_8Cl_3NO$: C, 29.34; H, 3.91; N, 6.85.

The infrared spectrum showed an NH band.

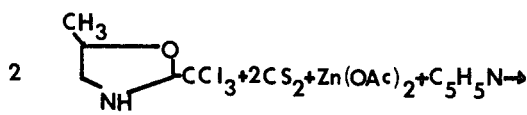

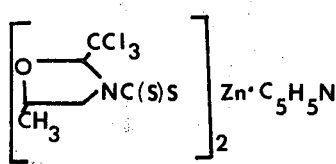

A mixture of 237.0 g. (3.0 moles) pyridine, 38.0 g. (0.50 mole) carbon disulfide, 45.9 g. (0.25 mole) anhydrous zinc acetate and 102.3 g. (0.50 mole) 5-methyl-2-trichloromethyloxazolidine was stirred for 3 hours at 45°C. After standing overnight at room temperature the reaction mixture was diluted with 1 liter of water. The insoluble oil layer was separated, treated with 200 ml. hot isopropanol, and cooled to 5°C. The precipitate was filtered off to give 103.5 g of crude product. It was dissolved in 450 ml. hot pyrdine; at 10°C. the pyridine solution was diluted with 1500 ml. water and filtered to give 53.8 g. of the desired product melting at 104°–133°C. with pyridine loss and decomposition. It had the following analysis:

Found: C, 29.29; H, 2.91; N, 6.17; Zn, 9.70. Calc. for $C_{12}H_{11}Cl_6N_2O_2S_4Zn \cdot C_5H_5N$: C, 29.00; H, 2.70; N, 5.97; Zn, 9.30.

EXAMPLE 20

Zinc Bis(5-methyl-2-trichloromethyloxazolidine-3-carbodithioate)

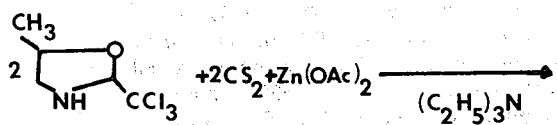

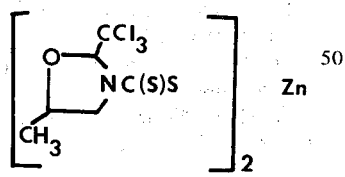

A mixture of 412.0 g. (4.0 moles) triethylamine, 60.8 g. (0.8 mole) carbon disulfide, 73.2 g. (0.4 mole) anhydrous zinc acetate and 163.6 g. (0.8 mole) 5-methyl-2-trichloromethyloxazolidine was stirred at 40°C. for 1 hour. After standing overnight at room temperature, the reaction mixture was diluted with water and filtered to give 417.8 g. of the desired crude product sintering at 89°C. and melting with decomposition at 128°–150°C. Extraction with chloroform and repeated crystallization from benzene gave an analytical sample melting at 170°–176°C. with decomposition. It had the following analysis:

Found: N, 4.30; Zn, 10.16. Calc. for $C_{12}H_{14}Cl_6N_2O_2S_4Zn$: N, 4.48; Zn, 10.47.

EXAMPLE 21

Zinc Bis(4,4-dimethyloxazolidine-3-carbodithioate)

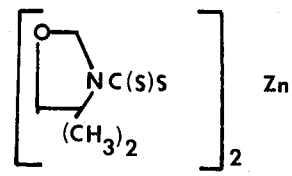

Thirty grams (1.0 mole) paraformaldehyde was added to a solution of 89.2 g. (1.0 mole) 2-amino-2-methyl-1-propanol in 600 ml. isopropanol, temperature at 45°–64°C. After all the paraformaldehyde had dissolved, the mixture was cooled to 12°C.; 92 g. (0.50 mole) anhydrous zinc acetate and 76 g. (1.0 mole) carbon disulfide was added. The reaction mixture was stirred six hours at 45°–50°C. Filtration at 5°C. gave 152.6 g. of the desired product melting with decomposition at 209°–211°C. A benzene-crystallized sample had the following analysis:

Found: C, 34.92; H, 4.91; N, 6.62; Zn, 15.47. Calc. for $C_{12}H_{20}N_2O_2S_4Zn$: C, 34.50; H, 4.79; N, 6.71; Zn, 15.67.

EXAMPLE 22

Zinc Bis(5-phenyl-3-oxazolidinecarbodithioate)

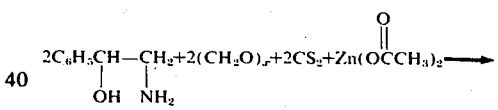

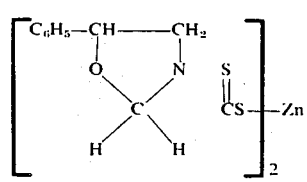

To 500 ml isopropanol was added 30 g. (1.0 mole) of paraformaldehyde and 137 g. (1.0 mole) of 2-amino-1-phenylethanol, and the resulting mixture was stirred and heated at 50°C. After the solids had all dissolved, the solution was stirred an additional 30 minutes at 50°C. To the solution, cooled to 35°C., was added 68.7 g. (0.375 mole) of anhydrous zinc acetate and 76.0 g. (1.0 mole) of carbon disulfide. Solids formed in several minutes whereby additional isopropanol (400 ml) was added to stir the mixture efficiently. After heating at 55°C. for 2 hours, the mixture was cooled and filtered; the resulting solids were washed several times in a Waring Blendor with water, and air-dried overnight to obtain 184 g (95%) of the desired product melting at 220°–223°C.; its IR spectrum was consistent with the structure.

Found: N, 4.90, Zn, 12.73. Calc. for $C_{20}H_{20}N_2O_2S_4Zn$: N, 5.45; Zn, 12.13.

EXAMPLE 23

Zinc Bis(5-phenyl-2-trichloromethyl-3-oxazolidinecarbodithioate)

$$2(C_2H_5)_3N+Zn(OCCH_3)_2+2 \quad \begin{array}{c} C_6H_5-CH \longrightarrow CH_2 \\ | \quad\quad\quad\quad | \\ O \quad\quad\quad NH \\ \backslash \quad / \\ C \\ / \quad \backslash \\ H \quad CCl_3 \end{array} \quad +2CS_2 \longrightarrow$$

$$\left[ \begin{array}{c} C_6H_5-CH \longrightarrow CH_2 \\ | \quad\quad\quad\quad | \\ O \quad\quad\quad N \quad S \\ \backslash \quad / \quad \backslash \parallel \\ C \quad\quad C \\ / \quad \backslash \quad / S \\ H \quad CCl_3 \end{array} \right]_2 Zn$$

A mixture of equimolar amounts of chloral, glacial acetic acid, and 2-amino-1-phenylethanol in benzene was refluxed using a Dean-Stark receiver until no more water was formed. The benzene was distilled off; the distillation residue was triturated with ether and filtered. The filtrate was evaporated to obtain the crude 5-phenyl-2-trichloromethyloxazolidine, m.p. 58°–65°C. Its structure was confirmed by its infrared spectrum and by elemental analysis of a sample melting at 67°–69°C. after recrystallization from ether.

A mixture of 30.3 g (0.3 mole) triethylamine, 13.3 g. (0.1 mole) zinc acetate, 55.0 g. (0.206 mole) 5-phenyl-2-trichloromethyloxazolidine and 15.6 g. (0.206 mole) carbon disulfide was stirred at ambient temperatures for 17 hours and then was heated at 50°C, for three hours. A reddish amber-colored semi-solid was obtained after the volatile materials were distilled off at 50°/25 mm. Hg. The semi-solid was dissolved in methanol and the resulting solution added to water with vigorous stirring. The solids were filtered, air-dried, and redissolved in benzene. After drying the solution with magnesium sulfate, filtering the mixture and evaporating the solvent, 37 g. (58%) of the desired product (m.p. 91°–93°C.) was obtained; its infrared spectrum was consistent with the structure.

Found: N, 3.86. Calc. for $C_{22}H_{18}Cl_6N_2O_2S_4Zn$: N, 3.74.

EXAMPLE 24

Zinc Bis (2-hexyl-2-methyl-3-oxazolidinecarbodithioate), Pyridine Adduct

To a solution of 22.8g (0.30 mole) carbon disulfide in 142.6g (1.8 moles) pyridine was added 76.0g (0.44 mole) crude 2-hexyl-2-methyloxazolidine [b.p. 75°–80°C., 6 mm. Hg (prepared from ethanolamine and 2-octanone by azeotroping with benzene, distilled, and used immediately) over a period of 5 minutes at a temperature of 15°–18°]. After the solution was stirred an additional five minutes, 25.7g (0.14 mole) anhydrous zinc acetate was added and the flask contents were allowed to stir at ambient temperatures for 16 hours. After the volatiles were removed under reduced pressure, the resulting pale-yellow solids were treated with methylene chloride. The organic layer was washed with 15 × 100 ml water (solids filtered off) and then stripped of solvent under reduced pressures to give a viscous oil. After triturating the oil with 600 ml low boiling (40°–60°) petroleum ether, the resulting yellow solid was extracted with ethyl ether; after removing the ether, 35g (39% conversion based on zinc acetate) white solid was obtained, m.p. 103°–6°C. A sample was recrystallized for analysis from ethyl ether (m.p. 105°–7°).

Analysis: Found: C, 50.63; H, 6.93; N, 6.47; S, 19.10; Zn, 10.16. Calcd. for $C_{22}H_{40}N_2O_2S_4Zn \cdot C_5H_5N$: C, 50.90; H, 7.11; N, 6.59; S, 20.09; Zn 10.26.

EXAMPLE 25

Triethylammonium 2-Trichloromethyl-3-oxazolidinecarbodithioate

A mixture of 114 g (0.60 mole) 2-trichloromethyloxazolidine, 121.2g. (1.2 moles) triethylamine and 68.4 g. (0.9 mole) carbon disulfide was heated at 50° for 7 hours and then was left standing for 18 hours at room temperature. The yellow solids were filtered, stirred with anhydrous ethyl ether, and filtered again to obtain 195.5 g (88.7% conversion) of the desired product, m.p. 107°–110°C.

Analysis: Found: C, 35.96; H, 5.69; N, 7.70. Calcd. for $C_{11}H_{21}Cl_3N_2OS_2$: C, 35.92; H, 5.75; N, 7.62.

EXAMPLE 26

Cadmium Bis (2-trichloromethyl-3-oxazolidinecarbodithioate)

$$\left[ \begin{array}{c} O \longrightarrow CCl_3 \\ | \quad\quad\quad \\ \quad\quad N-C(S)S \end{array} \right]_2 Cd$$

Cadmium acetate dihydrate (6.7g., 0.025 mole) was stirred into a solution of 18.4g. (0.050 mole) of triethylammonium 2-trichloromethyloxazolidine-3-carbodithioate in 300 ml. of 95% ethanol at 30°C. The precipitate was filtered off at 5°C. and water-washed on the filter. After drying in a vacuum desiccator, there was obtained 12.8 g. of white crystals, melting at 223°–225°C. with decomposition. Its infra-red spectrum confirmed the desired structure and was essentially the same as that of the corresponding zinc and copper salts.

Analysis: Found: C, 19.07; H, 1.97; N, 4.65. Calcd.: C, 18.65; H, 1.55; N, 4.35.

EXAMPLE 27

Cupric Bis (2-trichloromethyloxazolidine-3-carbodithioate)

$$\left[ \begin{array}{c} O \longrightarrow CCl_3 \\ | \quad\quad\quad \\ \quad\quad N-C(S)S \end{array} \right]_2 Cu$$

To a stirred suspension of 8.0g. (0.04 mole) of cupric acetate monohydrate in 400 ml. of 95% ethanol at 80°C was added a solution of 29.4g. (0.08 mole) of triethylammonium 2-trichloromethyloxazolidine-3-carbodithioate in 400 ml. of 95% ethanol over a 30-min. period. After evaporating under vacuum at room temperature to one tenth of its original volume, 3 liters of distilled water was added and the brown, insoluble product was filtered and washed on the filter with a little distilled water to give 19.3 g. of the desired product melting at 186°–188°C. with decomposition. A small sample for analysis was washed with hot chloroform. Its infra-red spectrum was in agreement with the structure of cupric bis(2-trichloromethyloxazolidine-3-carbodithioate).

Analysis: Found: C, 19.72; H, 1.81; N, 4.52. Calcd.: C, 20.18; H, 1.68; N, 4.70.

EXAMPLE 28

Triethylammonium 2-Phenyl-3-oxazolidinecarbodithioate

To a solution of 574g (5.68 moles) triethylamine and 422g (2.84 moles) 2-phenyloxazolidine (containing mainly the tautomer, N-benzylidene-2-hydroxyethylamine which was prepared according to the procedure of L. Daasch et al., J.A.C.S. 72, 3673 (1950)), was added 324g (4.26 moles) carbon disulfide at 19°–24° over a period of 40 minutes. Toward the latter part of the $CS_2$-addition a yellow oil formed. After 5 hours of vigorous stirring, the oil crystallized to a yellow solid within a short period whereby the temperature increased to 36°. The solids were transferred to a suitable flask to which was added 2 liters anhydrous ethyl ether, stirred vigorously and then filtered. After the trituration was repeated twice more, a quantitative yield of white solid product was obtained m.p. 73°–75°C. An analytical sample was prepared by dissolving the solid product in warm (40°) isopropanol, cooling to 25°, adding ethyl ether without precipitating the solid, cooling 0° to precipitate the solid, and then filtering and drying the resulting solid to give 282g (68% conversion) m.p. 75.5° – 77.5°C.

Anaylsis: Found: C, 58.9; H, 7.32; N, 8.23; S, 20.1. Calcd. for $C_{16}H_{26}N_2OS_2$: C, 58.9; H, 8.03; N, 8.56; S, 19.6.

EXAMPLE 29

Triethylammonium 3-Oxazolidinecarbodithioate

N, N', N'' - Tris (2-hydroxyethyl) hexahydro triazine (328g) was cracked at a vapor temperature of 74°–93°C and a pressure of 2–3 mm Hg to yield 292g (3.73 moles) oxazolidine contaminated with N-methylene-2-hydroxyethylamine (trapped at −50°). To the amine mixture, maintained at −50°, was added 600 ml toluene with stirring and 606g (6.0 moles) triethylamine. Carbon disulfide (456g, 6.0 moles) was added to the cold (−20° to −15°) solution in one hour, during which time solids formed. Stirring was continued an additional hour at 0° to −10° and then the mixture was filtered cold ($N_2$ atmosphere); the resulting solids were dried in a vacuum desiccator over NaOH to yield 335g (29.8% conversion based on the triazine white solid, m.p. 75°–85°C.

Analysis: Found: N, 11.0; S, 26.3. Calcd. for $C_{10}H_{22}N_2OS_2$: N, 11.2; S, 25.6.

EXAMPLE 30

Triethylammonium 2-Trichloromethyl-3-thiazolidinecarbodithioate

A mixture of 356 g (1.72 moles) 2-trichloromethyl-thiazolidine*, 347 g (3.44 moles) triethylamine and 261g (3.44 moles) carbon disulfide was stirred at ambient temperatures for 48 hours and then was filtered. The yellow-colored solid was washed with a minimum of ether and then dried under vacuum to give 152g (23% conversion) of product, m.p. 105°–5.5°C (melts with gas evol., solid forms) 160°–5° (dec, gas evol.)

B.J. Sweetman et al., J. Med. Chem. 12, 888 (1969)

Analysis: Found C, 35.1; H, 5.56; N, 7.08; S, 24.8. Calcd: $C_{11}H_{21}Cl_3N_2S_3$: C, 34.4; H, 5.51; N, 7.30; S, 25.0.

EXAMPLE 31

Triethylammonium 3-Thiazolidinecarbodithioate

To a solution of 70g (0.79 mole) thiazolidine ** and 160g (1.58 moles) triethylamine in 1 liter ethyl ether was added 120g (1.58 moles) carbon disulfide at 21°–2° over a period of 30 minutes. After the mixture was stirred at ambient temperatures for an additional 2.5 hours, it was filtered to give a pale yellow solid which was then washed with 1.5 l. (5 × 300ml) ether to yield 201g (96% conversion) of desired product, m.p. 101°–3°C. (gas evol.).

S. Ratner and H. Clarke, J.A.C.S. 59, 200 (1937).

Analysis: Found: C, 45.3; H, 8.16; N, 10.0; S, 36.6. Calcd. for $C_{10}H_{22}N_2S_3$: C, 45.1; H, 8.33; N, 10.5; S, 36.1.

EXAMPLE 32

Sodium 2-Trichloromethyl-3-oxazolidine-carbodithioate Polyhydrate

A mixture of 11.4 g (0.06 mole) 2-trichloromethyl-oxazolidine, 5.47g. (0.072 mole) carbon disulfide and 15.6g (0.06 mole) of 15% aq. sodium hydroxide was heated with stirring at 65°–70° for 17 hours. The reaction mixture was evaporated at 40°/mm Hg. The cooled residue was extracted with anhydrous ethyl ether to yield an extract (which was set aside and used below) and a yellow residual solid which was extracted with dry acetone. The volatiles were removed from the acetone extract to give a tacky solid which was then washed with a minimum of ether to yield 2.1g of yellow-orange product, m.p. 100°–120°(decomposition, gas).

The above etheral extract which had been set aside for 30 minutes produced yellow solids which was filtered. These solids were treated again with ether to yield a residual solid (slightly impure product) and an extract. Solids which formed in the extract were filtered to yield the yellow-orange crystalline product, m.p. 105°–9°C. (dec., gas).

Analysis: Found: C, 18.88; H, 3.30; Cl, 28.59; N, 4.07; S, 20.26. Calcd. for $C_5H_5Cl_3NNaOS_2 \cdot 2\frac{1}{2} H_2O$: C, 18.00; H, 3.02; Cl, 31.92; N, 4.20; S, 19.18.

In utilizing the compounds of this invention as accelerators in the vulcanization of elastomers, especially of ethylene-propylene-diene (EPDM) elastomers, generally from about 0.5 to 5 phr., preferably 1.5 to 4 phr., of accelerator-compound are used, usually with from about 0.5 to 3 phr. of sulfur as the vulcanization agent. (phr. means parts per 100 parts by weight of the elastomer). The accelerator composition is milled into the elastomer along with the sulfur, and other optional modifying ingredients, for example, carbon black, stearic acid, zinc oxide, naphthenic oil, and others known to the trade. The elastomer is then normally cured (vulcanized) by heating to from about 300° to 450°F for from about 10 seconds to one hour, usually for about 10 – 40 minutes at about 300° – 350°F.

It has been observed that the compounds of the present invention not only retard blooming in the cured elastomers but also generally show increased accelerator activity as demonstrated by a significant increase in elastomer tensile strength and modulus when comparisions are made at equivalent concentrations of related accelerators and the same curing conditions. The results of the invention, in particular the unexpected nature of the non-blooming characteristic, is demonstrated by reference to the following examples in which the vulcanization evaluations of a representative EPDM elastomer using both claimed and comparative accelerator compositions are carried out. The following recipe is used, where the amounts of ingredients are based on parts by weight per 100 parts of elastomer.

|  | Parts by Weight |
|---|---|
| EPDM elastomer (ethylene-propylene-dicyclopentadiene terpolymer | 100 |
| Naphthenic oil | 50 |
| Carbon (FEF) black | 100 |
| Zinc oxide | 5 |
| 2-Mercaptobenzothiazole | 0.5 |
| Stearic acid | 2 |
| Sulfur | variable, 0.5 and 2 |
| Accelerator | variable, 2 and 4 |

The curing of vulcanizate is carried out at 320°F., removing samples for testing at 5, 10, 20, 30, 40 and 60 minutes intervals.

In Table 1, below, are listed the various representative compounds evaluated as accelerators. Accelerators Numbers 1 through 9, 13, 16, 18 through 23, 25 through 33 are embodied in this invention. Particularly preferred accelerators are those identified as Nos. 1, 2, 3, 4, 8 18, 22 and 23. Comparative accelerators tested include zinc dithiocarbamates which have a structure somewhat similar to the compounds of the present invention, e.g., accelerator No. 10 is a commercial ultra-accelerator for elastomers. Other salts of dithiocarbamic acid, e.g., accelerators No. 12 and No. 17, and zinc salts of other acids, e.g., accelerator No. 11, are also known accelerators, two of which are commercial. The physical data for the observations on blooming are presented in Tables 2 and 3.

The results establish that, in contrast to the accelerators of this invention, previously known accelerators 10–12 and 17 cause blooming. Blooming is also encountered in the use of spiro-compounds and 4,4-disubstituted compounds, represented by accelerators No. 14 and No. 24, respectively, and the zinc salt of the reaction product of ethanolamine, formaldehyde and carbon disulfide (disclosed in the aforementioned U.S. Pat. No. 3,674,701), represented by accelerator No. 15. In addition, the spiro-compound is not very effective as an accelerator. The compounds of this invention are shown to be not only effective non-blooming accelerators but in several cases are even faster than the present commercial ultra accelerators; for example, compare No. 1 with No. 12; No. 3, No. 8, No. 22 and No. 23 with No. 10 and No. 12.

TABLE NO. 1

Representative Accelerators Tested in EPDM Elastomer

| Example No. | Accelerator No. |  |
|---|---|---|
| 2 | 1. | Zinc Bis(3-oxazolidinecarbodithioate) |
| 3 | 2. | Zinc Bis(2-trichloromethyl-3-oxazolidine-carbodithioate) |
| 4 | 3. | Zinc Bis(2-trichloromethyl-3-oxazolidine-carbodithioate), Pyridine Adduct |
| 5 | 4. | Zinc Bis(2,2-dimethyloxazolidine-3-carbodithioate) |
| 7 | 5. | Zinc Bis[2-(p-dimethylaminophenyl)oxazolidine-3-carbodithioate], Pyridine Adduct |
| 6 | 6. | Zinc Bis[2-(3-ethoxy-4-hydroxyphenyl)oxazolidine-3-carbodithioate], Tripyridine Adduct |
| 8 | 7. | Zinc Bis(thiazolidine-3-carbodithioate) |
| 9 | 8. | Zinc Bis[(2-trichloromethyl)thiazolidine-3-carbodithioate], Dipyridine Adduct |
| 10 | 9. | Zinc Bis(2,2-dimethylthiazolidine-3-carbodithioate) |
|  | 10. | Zinc Bis(diethyldithiocarbamate) |
|  | 11. | Zinc Bis(O,O-dibutyl phosphorodithioate) |
|  | 12. | Tellurium Tetrakis(diethyldithiocarbamate) |
| 24 | 13. | Zinc Bis (2-hexyl-2-methyl-3-oxazolidine-carbodithioate), Pyridine Adduct |
| 11 | 14. | Zinc Bis[spiro(cyclohexane-1,2'-oxazolidine)-3-carbodithioate] |
| 12 | 15. | Zinc salt of the reaction product of ethanolamine, formaldehyde and carbon disulfide |
| 13 | 16. | Zinc Bis(2-methyl-2-phenyloxazolidine-3-carbodithioate), Pyridine Adduct |
| 14 | 17. | Zinc Bis(4-morpholinecarbodithioate) |
| 15 | 18. | Zinc Bis(2-phenyloxazolidine-3-carbodithioate), Pyridine Adduct |
| 16 | 19. | Zinc Bis(2-phenyloxazolidine-3-carbodithioate) |
| 17 | 20. | Zinc Bis[2-(p-chlorophenyl)oxazolidine-3-carbodithioate], Pyridine Adduct |
| 18 | 21. | Zinc Bis[2-(1-ethylpentyl)oxazolidine-3-carbodithioate], Pyridine Adduct |
| 19 | 22. | Zinc Bis(5-methyl-2-trichloromethyloxazolidine-3-carbodithioate), Pyridine Adduct |
| 20 | 23. | Zinc Bis(5-methyl-2-trichloromethyloxazolidine)-3-carbodithioate) |
| 21 | 24. | Zinc Bis(4,4-dimethyloxazolidine-3-carbodithioate) |

TABLE NO. 1-continued

| Example No. | Accelerator No. | Representative Accelerators Tested in EPDM Elastomer |
|---|---|---|
| 22 | 25. | Zinc Bis(5-phenyl-3-oxazolidinecarbodithioate) |
| 23 | 26. | Zinc Bis(5-phenyl-2-trichloromethyl-3-oxazolidine-carbodithioate) |
| 25 | 27. | Triethylammonium 2-trichloromethyl-3-oxazolidinecarbodithioate. |
| 26 | 28. | Cadmium Bis(2-trichloromethyl-3-oxazolidinecarbodithioate) |
| 27 | 29. | Cupric Bis(2-trichloromethyl-3-oxazolidinecarbodithioate) |
| 28 | 30. | Triethylammonium 2-Phenyl-3-oxazolidinecarbodithioate |
| 29 | 31. | Triethylammonium 3-Oxazolidine-carbodithioate |
| 30 | 32. | Triethylammonium 2-Trichloromethyl-3-thiazolidinecarbodithioate |
| 31 | 33. | Triethylammonium 3-Thiazolidine-carbodithioate |

TABLE NO. 2

Vulcanizate (320°F)[a] with 2 phr of Accelerator and 2 phr of Sulfur

| Accelerator No.[b] | Example No. | Tensile (psi) at cure time (min.) | | | | | Modulus, 200% (psi) at cure time (min.) | | | | Bloom after 1–2 weeks |
|---|---|---|---|---|---|---|---|---|---|---|---|
| | | 5 | 10 | 20 | 40 | 60 | 5 | 10 | 20 | 40 | |
| 1 | 2 | 1390 | 2100 | 2640 | 2700 | 2775 | 500 | 725 | 1080 | 1400 | None |
| 2[c] | 3 | 1300 | 2175 | 2625 | 2800 | 2825 | 850[d] | 1300[d] | 2250[d] | 2775[d] | None |
| 3 | 4 | 1950 | 2310 | 2350 | 2475 | 2440 | 750 | 1050 | 1350 | 1470 | None |
| 5 | 7 | — | 875 | 1175 | 1600 | 2050 | — | 400 | 475 | 800 | None |
| 6 | 6 | 890 | 1250 | 1700 | 2150 | 2300 | 450 | 600 | 850 | 1090 | None |
| 7 | 8 | 620 | 1030 | 1540 | 2450 | 2550 | 350 | 550 | 900 | 1600 | None |
| 8 | 9 | 1600 | 2250 | 2600 | 2800 | 2900 | 675 | 1000 | 1350 | 1575 | None |
| 9 | 10 | 750 | 1000 | 1400 | 1775 | 1975 | 400 | 450 | 725 | 875 | None |
| 10 | — | 1325 | 2175 | 2800 | 2950 | 2750 | 550 / 850[d] | 850 / 1375[d] | 1375 / 2000[d] | 1650 / 2600[d] | Medium |
| 11 | — | 690 | 1140 | 2000 | 2490 | 2490 | 300 | 500 | 900 | 1220 | Light |
| 12 | — | 930 | 1650 | 2250 | 2675 | 2650 | 360 / 580[d] | 600 / 975[d] | 960 / 1500[d] | 1240 / 1950[d] | Light |
| 13 | 24 | 950 | 1610 | 2225 | 2600 | 2545 | 450 | 700 | 1000 | 1400 | None |
| 14 | 11 | Poor | Poor | 1175 | 1225 | 1475 | Poor | Poor | 850[d] | 950[d] | Light |
| 15 | 12 | 1360 | 2300 | 2600 | 2750 | 2625 | 550 | 950 | 1290 | 1420 | Light |
| 16 | 13 | 1250 | 1900 | 2575 | 2675 | 2650 | 525 | 800 | 1200 | 1700 | None |
| 18 | 15 | 1650 | 2190 | 2500 | 2550 | 2690 | 660 | 950 | 1200 | 1350 | None |
| 19 | 16 | 1150 | 1800 | 2150 | 2250 | 2350 | 490 | 800 | 1160 | 1400 | None |
| 20 | 17 | 1270 | 2010 | 2400 | 2490 | 2460 | 550 | 865 | 1120 | 1300 | None |
| 21 | 18 | 1210 | 1950 | 2475 | 2540 | 2725 | 500 | 760 | 1110 | 1450 | None |
| 22 | 19 | 1840 | 2270 | 2450 | 2540 | 2610 | 750 | 1010 | 1225 | 1420 | None |
| 23 | 20 | 2045 | 2420 | 2425 | 2410 | 2600 | 950 | 1175 | 1460 | 1660 | None |
| 24 | 21 | 1610 | 2290 | 2450 | 2690 | 2700 | 650 | 915 | 1400 | 1680 | Heavy |
| 25 | 22 | 750 | 1360 | 1990 | 2150 | 2250 | 400 | 660 | 990 | 1300 | None |
| 26 | 23 | 1720 | 2200 | 2450 | 2450 | 2600 | 810 | 1070 | 1380 | 1600 | None |
| 27 | 25 | 1110 | 1400 | 1675 | 2000 | 2100 | 450 | 700 | 1000 | 1400 | None |
| 28 | 26 | 875 | 1750 | 2375 | 2475 | 2600 | 425 | 800 | 1200 | 1600 | None |
| 29 | 27 | 810 | 1700 | 2220 | 2360 | 2570 | 400 | 750 | 1140 | 1525 | None |
| 30 | 28 | 1350 | 1975 | 2375 | 2250 | 2400 | 625 | 900 | 1175 | 1225 | None |
| 31 | 29 | 1200 | 1650 | 1875 | 2150 | 2225 | 600 | 800 | 825 | 1050 | None |
| 32 | 30 | 925 | 1275 | 1475 | 1925 | 1825 | 425 | 625 | 825 | 975 | None |
| 33 | 31 | 700 | 1100 | 1550 | 1875 | 2150 | 400 | 500 | 785 | 850 | None |

[a]except where marked with (c).
[b]see Table No. 1 for names of accelerators.
[c]cure temperature was 305°F instead 320°F;
[d]300% modulus

TABLE NO. 3

Vulcanize (320°F)[a] with 4 phr of Accelerator and 0.5 phr of Sulfur

| Accelerator No.[b] | Example No. | Tensile (psi) at cure time (min.) | | | | | Modulus, 200% (psi) at cure time (min.) | | | | Bloom after 1–2 weeks |
|---|---|---|---|---|---|---|---|---|---|---|---|
| | | 5 | 10 | 20 | 40 | 60 | 5 | 10 | 20 | 40 | |
| 1 | 2 | 780 | 1290 | 1900 | 2000 | 1980 | 300 | 430 | 690 | 750 | None |
| 2[c] | 3 | 800 | 1375 | 1975 | 2400 | 2450 | 575[d] | 850[d] | 1400[d] | 1650[d] | None |
| 4 | 5 | 1010 | 1875 | 2080 | 2250 | 2120 | 500 | 750 | 950 | 960 | None |
| 6 | 6 | 600 | 820 | 910 | 890 | 890 | 300 | 350 | 450 | 400 | None |
| 7 | 8 | — | 700 | 1060 | 1460 | 1510 | — | 350 | 500 | 700 | None |
| 8 | 9 | 1000 | 1550 | 2010 | 1950 | 1870 | 400 / 660[d] | 650 / 1010[d] | 850 / 1300[d] | 860 / 1310[d] | None |
| 10 | — | 1200 | 1980 | 2300 | 2375 | 2210 | 480 / 780[d] | 775 / 1240[d] | 990 / 1500[d] | 1000 / 1550[d] | Heavy |
| 11 | — | 790 | 1025 | 1510 | 1890 | 1775 | 350 | 440 | 600 | 750 | Light |
| 12 | — | 770 | 1450 | 1820 | 1850 | 1800 | 310 | 610 | 690 | 760 | Medium |
| 13 | 24 | 850 | 1300 | 1810 | 1930 | 1950 | 390 | 560 | 750 | 850 | None |
| 14 | 11 | Poor | Poor | Poor | 475 | 500 | Poor | Poor | Poor | 350 | Light |
| 15 | 12 | 775 | 1250 | 1550 | 1450 | 1570 | 380 | 600 | 650 | 650 | Light |

TABLE NO. 3-continued

| Accelerator No.[b] | Example No. | Vulcanize (320°F)[a] with 4 phr of Accelerator and 0.5 phr of Sulfur | | | | | | | | | Bloom after 1-2 weeks |
|---|---|---|---|---|---|---|---|---|---|---|---|
| | | Tensile (psi) at cure time (min.) | | | | | Modulus, 200%, (psi) at cure time (min.) | | | | |
| | | 5 | 10 | 20 | 40 | 60 | 5 | 10 | 20 | 40 | |
| 16 | 13 | 1230 | 1700 | 2000 | 1925 | 2050 | 500 | 690 | 850 | 875 | None |
| 17 | 14 | Poor | Poor | 630 | 940 | 1050 | Poor | Poor | 250 | 400 | Light |
| 18 | 15 | 1250 | 1650 | 1710 | 1630 | 1690 | 550 | 725 | 725 | 725 | None-Trace |
| 20 | 17 | 1250 | 1620 | 1700 | 1590 | 1580 | 600 | 660 | 710 | 700 | None |
| 21 | 18 | 1100 | 1600 | 1830 | 1900 | 500 | 550 | 780 | 760 | None | |
| 22 | 19 | 1460 | 1900 | 2050 | 2000 | 1890 | 570 | 800 | 900 | 900 | None |
| 23 | 20 | 1310 | 1840 | 2100 | 2040 | 2240 | 550 | 790 | 1000 | 1040 | None |
| 24 | 21 | 1160 | 1825 | 2050 | 2190 | 2125 | 500 | 800 | 950 | 950 | Heavy |
| 26 | 23 | 1300 | 1700 | 1800 | 1675 | 1675 | 590 | 800 | 840 | 850 | None |
| 27 | 25 | 1025 | 1100 | 1200 | 1200 | 1200 | 425 | 450 | 500 | 575 | None |
| 28 | 26 | — | — | 1500 | 1900 | 1900 | — | — | 625 | 800 | None |
| 29 | 27 | — | 750 | 1025 | 1410 | 1410 | — | — | 475 | 700 | None |

[a]except where marked with (c);
[b]see Table No. 1 for names of accelerators;
[c]cure temperature was 305°F instead of 320°F;
[d]300% modulus.

We claim:
1. A compound of the structure

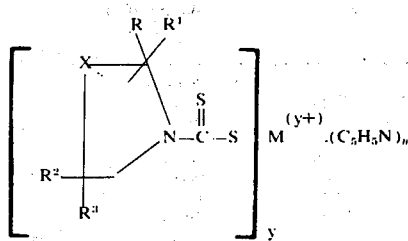

where X is sulfur or oxygen, R, $R^1$, $R^2$ and $R^3$ are independently selected from the group consisting of hydrogen, lower alkyl having from 1 to 8 carbon atoms, $CCl_3$, phenyl and substituted phenyl wherein there are not more than two substituents selected from the group consisting of $NR^4R^5$, OH, $OR^6$ and Cl where $R^4$ and $R^5$ are independently selected from the group consisting of hydrogen and methyl, $R^6$ is a lower alkyl having from 1 to 8 carbon atoms, not more than one of R and $R^1$ is phenyl or substituted phenyl and not more than one of $R^2$ and $R^3$ is phenyl or substituted phenyl; $C_5H_5N$ represents a pyridine molecule and n is an integer of 1 to 3; M is selected from the group consisting of Zn, Cd, Cu and Fe; and y is an integer of 1 to 3 corresponding to the valency of M.

2. A compound according to claim 1 wherein X is sulfur.

3. A compound according to claim 1 wherein X is oxygen.

4. A compound according to claim 1 wherein R, $R^1$, $R^2$ and $R^3$ are each hydrogen, X is oxygen, M is Zn and y is 2.

5. A compound according to claim 1 wherein R is hydrogen, $R^1$ is $CCl_3$, $R^2$ and $R^3$ are each hydrogen, X is sulfur, M is Zn and y is 2.

6. A compound according to claim 1 wherein R is hydrogen, $R^1$ is $CCl_3$, $R^2$ and $R^3$ are each hydrogen, and X is oxygen, M is Zn and y is 2.

7. A compound according to claim 1 wherein R, $R^1$, $R^2$ and $R^3$ are each hydrogen, X is oxygen, M is Cd and y is 2.

8. A compound according to claim 1 wherein R, $R^1$, $R^2$ and $R^3$ are each hydrogen, X is oxygen, M is Cu and y is 2.

9. A compound according to claim 1 wherein R, $R^1$, $R^2$ and $R^3$ are each hydrogen, X is sulfur, M is Cd and y is 2.

10. A compound according to claim 4 wherein n is 1.

11. A compound according to claim 1 wherein R, $R^1$, $R^2$ and $R^3$ are each hydrogen, X is sulfur, M is Zn and y is 2.

12. A compound according to claim 1 wherein R, $R^1$, $R^2$ and $R^3$ are each hydrogen, X is sulfur, M is Cu and y is 2.

13. A compound according to each claim 11 wherein n is 1.

14. A compound according to claim 5 wherein n is 2.

15. A compound according to claim 1 wherein R is hydrogen, $R^1$ is $CCl_3$, $R^2$ is hydrogen, $R^3$ is methyl, X is oxygen, M is Zn and y is 2.

* * * * *

UNITED STATES PATENT OFFICE
CERTIFICATE OF CORRECTION

Patent No. 3,976,648            Dated August 24, 1976

Inventor(s) Ivan Chistoff Popoff et al.

It is certified that error appears in the above-identified patent and that said Letters Patent are hereby corrected as shown below:

Column 24, lines 45-46 should read:
--- 13. A compound according to claim 11 wherein n is 1. ---

Signed and Sealed this

Fourth Day of January 1977

[SEAL]

Attest:

RUTH C. MASON
*Attesting Officer*

C. MARSHALL DANN
*Commissioner of Patents and Trademarks*